US006216388B1

(12) United States Patent
Miller et al.

(10) Patent No.: US 6,216,388 B1
(45) Date of Patent: *Apr. 17, 2001

(54) DISSOLVING POLYMER PLUG FOR INTRODUCING NUTRIENTS AND MEDICINAL MATERIALS INTO TREE TRUNKS

(76) Inventors: Gene W. Miller, 935 South 400 East, Providence; Salam Awada, 385 West 790 South, Logan, both of UT (US) 84321

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/056,169

(22) Filed: Apr. 7, 1998

(51) Int. Cl.[7] .......................... A01N 25/08; A01N 25/34; B27B 25/00
(52) U.S. Cl. .......................... 47/57.5; 47/58.1; 424/405; 424/409; 424/422; 424/426
(58) Field of Search ..................................... 47/57.5, 58.1; 424/405, 409, 422, 426, DIG. 8, DIG. 15, 78.08, 78.37; 514/772.3

(56) References Cited

U.S. PATENT DOCUMENTS

| | | |
|---|---|---|
| 3,304,655 | 2/1967 | Mauget . |
| 3,582,260 * | 6/1971 | Gersonde et al. ................... 118/50 |
| 3,706,161 | 12/1972 | Jenson . |
| 3,864,874 * | 2/1975 | Norris et al. ........................ 47/57.5 |
| 3,912,752 | 10/1975 | Meiser et al. . |
| 3,932,613 * | 1/1976 | Chapura ............................... 424/78 |
| 4,342,176 | 8/1982 | Wolfe . |
| 4,344,250 * | 8/1982 | Fahlstrom ........................... 47/57.5 |
| 4,368,185 * | 1/1983 | Mizuno et al. ..................... 424/436 |

(List continued on next page.)

FOREIGN PATENT DOCUMENTS

| | | |
|---|---|---|
| 56-025101 | 3/1981 | (JP) . |
| 62-42902 * | 2/1987 | (JP) . |
| 8-175914 * | 7/1996 | (JP) . |

OTHER PUBLICATIONS

North, C.P., 1986. Technique of injecting substances into Woody plants. pp. 138–142. In a Decade of synthetic chelating agents in Inorganic plant nutrition. A. Wallace (ed), Los angeles, California.

Wallace, G.A and A. Wallace. Correctionof iron deficiency in trees by injection with ferric ammonium citrate solution. Journal of plant nutrition 9 (3–7), pp. 981–986. 1986.

Budavari, S., 1989. , The Merck Index: An encyclopedia of chemicals, drugs, and biologicals. 11th ed. pp. 685 Merck and Co., Inc. Rahway, N.J., U.S.A.

Budavari, S ., 1989. The Merck Index: an encyclopedia of chemicals, drugs, and biologicals. 11th ed. pp. 1204 Merck and Co., Inc. Rahway, N.J., U.S.A.

Gao, K. 1993. Polyethylene Glycol as an embedment for Microscopy and Histochemistry. CRC press pp. 1–7 Ann Arbor, Michigan.

Chemical Absracts Assession No. 95:1914.*

*Primary Examiner*—Robert H. Harrison
(74) *Attorney, Agent, or Firm*—Mallinckrodt & Mallinckrodt; Brian R. Rayve; A. Ray Osburn

(57) ABSTRACT

A method of introducing treatment agents comprising medicine or nutrients into a tree, involving the boring of holes above ground into the trunk of the tree. Homogeneous plugs of solidified polyethylene glycol (PEG) with such treatment agents mixed therein are molded and inserted into the holes in the tree trunk and sealed with wax. The dissemination time of the treatment agent into the tree trunk is controlled by selection of the PEG's used, with higher molecular weights PEG's taking longer to dissolve and disseminate the treatment agent into the transpirational flow of the tree being treated than the lower molecular weight PEG's. The method leaves no foreign material such as plastic casings or cartridges within the tree trunk after treatment.

12 Claims, 2 Drawing Sheets

U.S. PATENT DOCUMENTS

Figure 5:
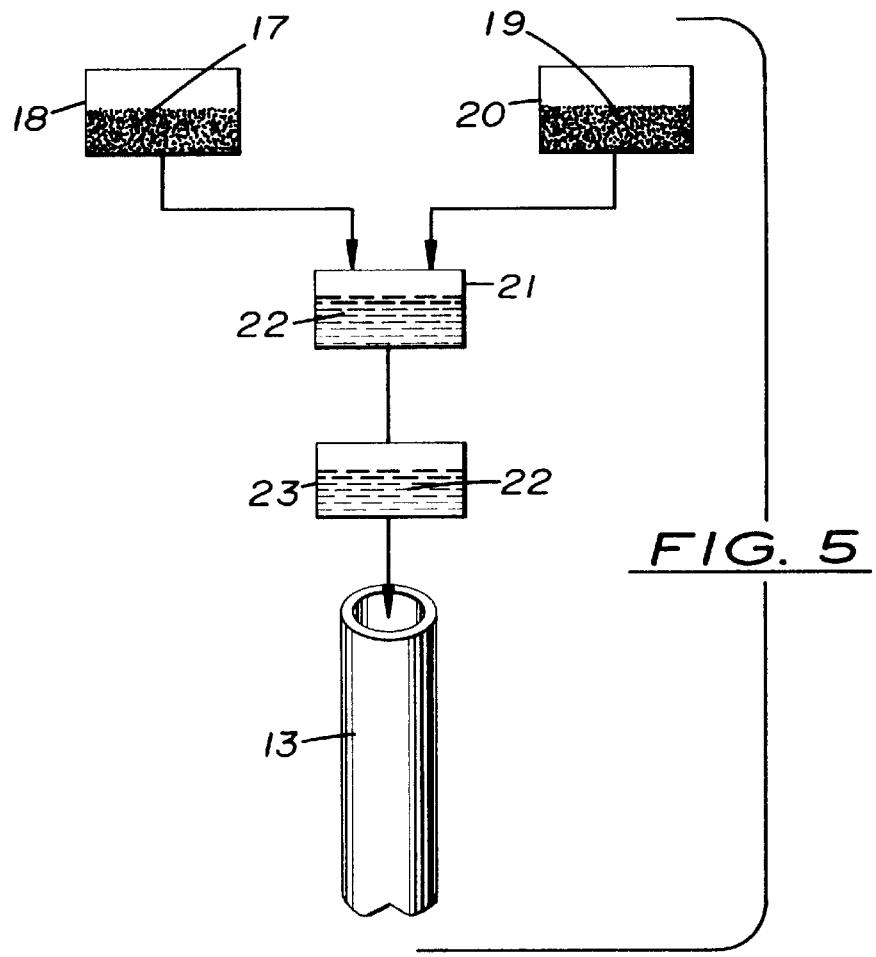

| | | | |
|---|---|---|---|
| 4,462,984 | * | 7/1984 | Mizuno et al. .................... 514/772.7 |
| 4,989,366 | * | 2/1991 | DeVlieger .............................. 47/57.5 |
| 5,104,664 | | 4/1992 | Palmere et al. . |
| 5,296,240 | * | 3/1994 | Palmere et al. ....................... 424/660 |
| 5,461,824 | | 10/1995 | Cassell . |
| 5,506,001 | * | 4/1996 | Ma et al. .............................. 427/408 |
| 5,597,840 | | 1/1997 | Moore . |
| 5,645,828 | * | 7/1997 | Palmere et al. .................... 424/78.08 |
| 5,956,894 | * | 9/1999 | Eldridge ................................ 47/57.5 |
| 6,032,411 | * | 3/2000 | Foust ..................................... 47/57.5 |

* cited by examiner

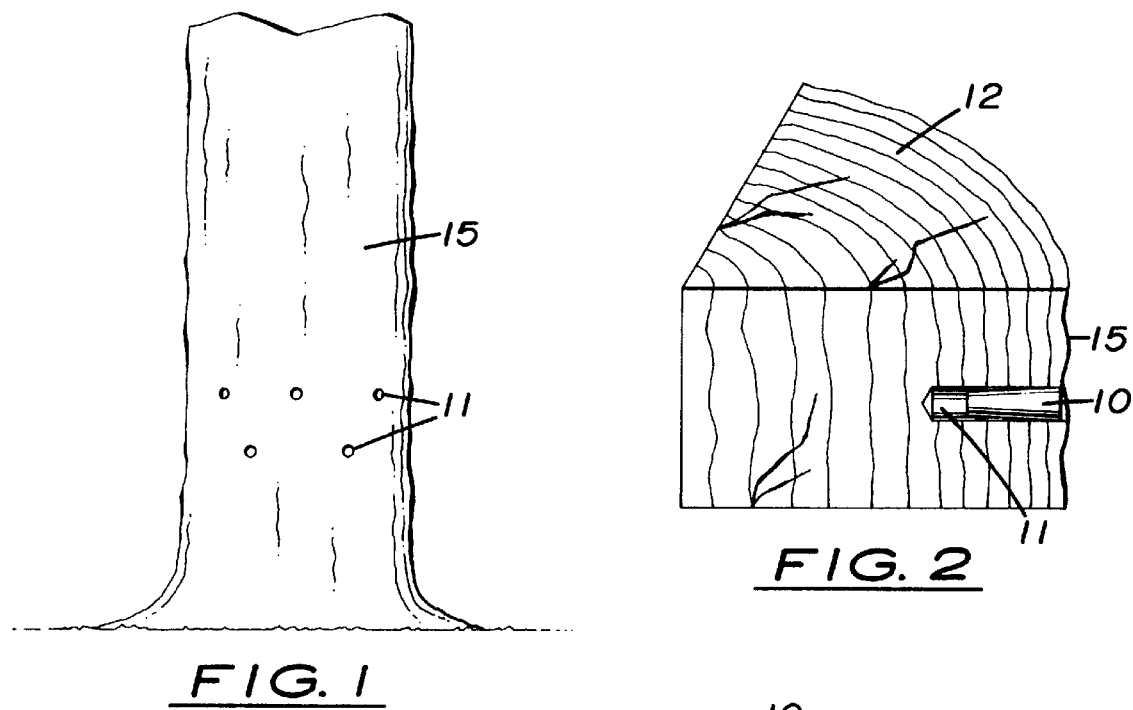
FIG. 1
FIG. 2
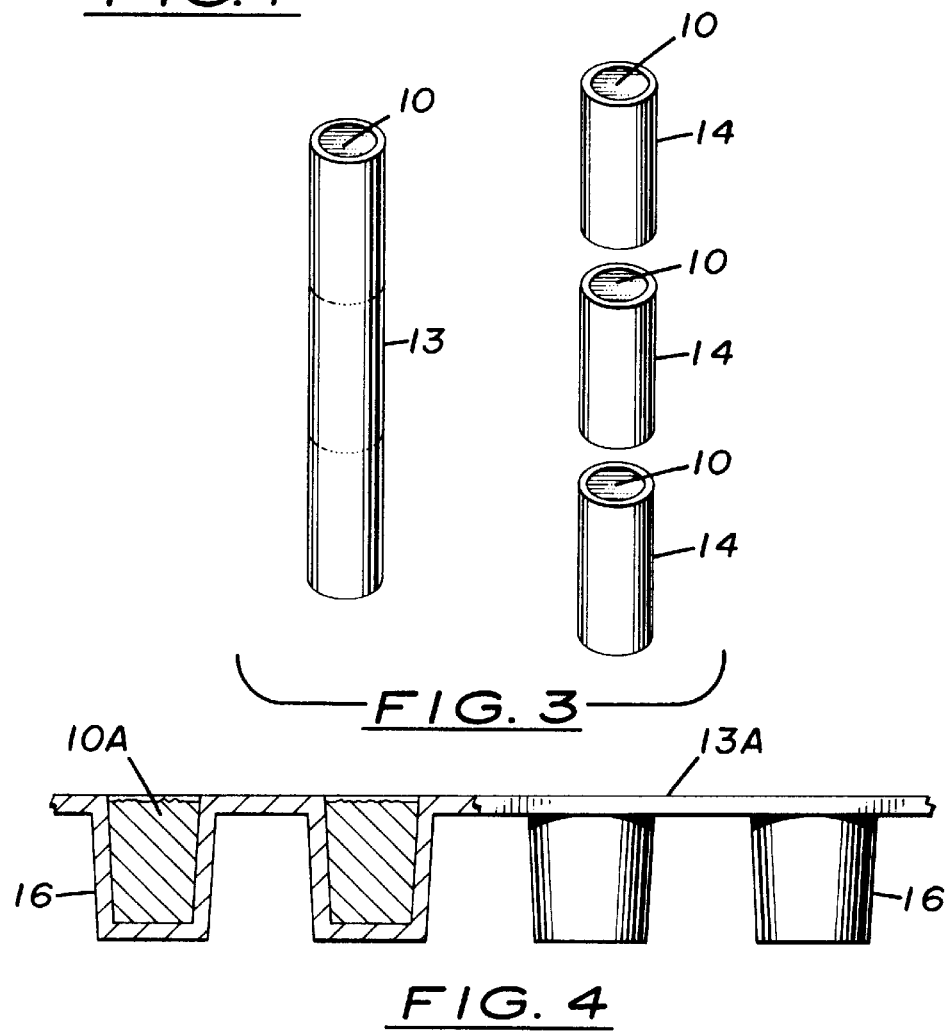
FIG. 3
FIG. 4

DISSOLVING POLYMER PLUG FOR INTRODUCING NUTRIENTS AND MEDICINAL MATERIALS INTO TREE TRUNKS

BACKGROUND OF THE INVENTION

1. Field

The field of the invention is fertilization of nutrient deficient trees and treatment of diseased trees, respectively.

2. State of the Art

Obtaining optimum food production from soil and other plant growing mediums is largely a problem of providing proper nutrition for production of increased biomass of the plants. Although green plants, being true autotrophs, supply the many organic components necessary for growth through photosynthesis, oxygen, carbon, hydrogen, and 13 known minerals are nevertheless required for lifetime development. However, nutrients present in the soil are not available to the plant unless in suitable chemical form, and various related soil and nutrient factors are also involved. Paramount among these are the concentrations of the nutrient in the soil, the solubility of the nutrient when present, its cation charge capacity, the root form and structure of the plant being grown, the texture and structure of the soil, the atmosphere, and the acidity or alkalinity of the soil.

Natural soils vary with respect to these growth influencing factors. For example, the productivity of desert and short grass prairie soils in the western United States is only one or two percent the productivity of wet lands in Georgia. Although this is partially the result of low rainfall in the west, poor soil fertility and structure are also involved.

The addition of missing nutrients to the soils has been long practiced with beneficial results. However, current practices, generally the simple addition of fertilizers to soils, may be very wasteful, unnecessarily expensive, inefficient in terms of plant utilization, and even detrimental to the environment. A significant amount of fertilizer is lost directly through leaching and is not available when needed during the growing period. Sometimes the nutrient becomes captured in insoluble compounds and is unavailable for plant utilization. Essential nitrogen fixing bacteria and mycorrhizai fungi may be lacking, which are very important to root growth for healthy plant growth. Another common problem is application of excess quantities of nutrient salts, resulting in plant "burn", with stunted growth or even death of the plant.

These problems have caused consideration of more sophisticated methods of providing nutrient treatment agents to the deficiently nourished plants. One approach is to bypass the soil solubility problem and to instead supply iron directly to the above ground parts of the plants such as the direct foliar application of the nutrients. Foliar sprays of iron compounds have been demonstrated to increase greening of leaf and stem tissues. A problem with this procedure is the limited penetration of the iron from the leaf surface into the chloroplast. The inclusion of a wetting agent and/or a carrying compound in the spray increases surface dispersion of spray droplets to enhance absorption. Such inclusion minimizes the "green island spotting" commonly observed with foliar iron application. This procedure requires repeated application throughout the season, since both new and existing growth require nutritive aid.

In addition to soil application and foliar spray application of iron compounds, lime-induced chlorosis in trees has for many decades been treated by introduction of iron compounds directly into the trunks of trees so effected. One method involves implantation of solid iron salts or of liquid injector devices into shallow holes bored into the trunk of the chlorotic tree. A number of forms of iron have been used, among them ferrous sulfate and ferrous citrate. The iron passes into solution in the tree trunk and moves to the foliage by way of the transpirational stream of the tree. In oak and white pine trees, application has noted beneficial effects of such treatment, but phytotoxicity and necrosis at the site of injection has been reported in susceptible species like citrus trees. It is often difficult to control the dissolution rate and concentration of iron going into the tissue of the tree trunk, which results often in tissue damage.

Prior investigators have implanted capsules which include various treatment agents into the tree trunk to correct mineral deficiencies and diseases in trees. (U.S. Pat. Nos. 3,706,161; 3,912,752; and 3,304,655).

Figure 6:
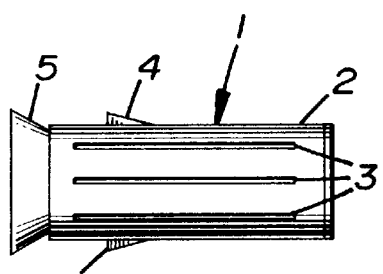

One such implant which is shown in prior art FIG. 6 comprises a cartridge 1 having a hollow body 2 in which a capsule (not shown) of cellulose or gelatin containing the treatment agent is disposed. A plurality of slits 3 allow the treatment agent in the capsule to migrate into the tree trunk upon insertion into a hole bored into the tree trunk. A plurality of spring-locking tabs 4 retain the cartridge within the hole in the tree trunk and a cap 5 of sealing wax seals the hole. Such gelatin capsules are not water soluble under normal temperature and conditions, although they are soluble in hot water (Budavari, S., 1989. The Merck Index, p. 685) and as such restrict the passage of treatment agent into the tree. No practical method of implanting capsules so as to attain needed concentrations of nutrients, fungicides or other treatment agents to control diseases has been achieved. Such cartridges containing a cellulose or gelatin capsule release the treatment agent at irregular rates and leave the non-degradable plastic cartridge inside the tree trunk tissue and residues of the treatment agent remain in the gelatin capsule. Also, gelatin capsules are insoluble in water at temperature below 35–40° C. and are insoluble in organic solvents (Budavari, S., 1989. The Merck Index, pp 685). The sap in the tree trunk tissue does not use up all the treatment agent before the injection hole is sealed off by callus tissue. Only water soluble chemicals can be used in this method to treat the tree. This is a limitation for pesticides since most are of limited solubility (e.g. dimetholate) or insoluble in water. As will be explained subsequently, the main component used in the present invention is widely used in the chemical industry as a solvent for many chemicals that are insoluble in water, which makes it advantageous over these prior art methods.

Another method of introducing treatment agents into a tree trunk is direct injection such as by means of a plastic injection syringe 6, (Prior Art FIG. 7) which contains a liquid (not shown) containing a treatment agent for injection into the tree trunk through an attached tube 8 when a piston 9 is depressed and locked. Such injection syringes 6 contain only small amounts of fluid and must be spaced every 5–6 inches around the trunk of the tree. Growers must remove the syringes after a few hours or a few days of treatment which is time consuming. Also, the cost of the injection syringes greatly exceeds that of the injection material. Direct injection of liquids is highly labor-consuming, since the injectors must be removed after a few hours or the next day after they are empty. Where a liquid pesticide is used, the injectors require special handling, and need to be disposed of in an environmentally safe place. Accordingly, they cannot be used in residential areas because the injector is completely exposed, only the injector tube or nozzle being inserted into the tree, with the cylinder containing the liquid outside and exposed. However, such method has been found particularly effective in arid and semi-arid areas, especially where the soils are calcareous wherein a growing tree is unable to utilize the iron in the soil. The direct injection of iron compounds into the trunk of the tree often effectively corrects the iron deficiency for a full growing season.

Another method of introducing a treatment agent into a tree trunk has been reported by North (1962) pp. 138–142 and Wallace and Wallace (1986) pp. 981–986. A hole is bored into the tree trunk and a reservoir of liquid including a treatment agent is attached. The treatment agent flows into the tissue and is translocated within the tree. This method is likely to produce an extensive necrotic area. Liters of liquid may be required, and concentrated liquids may be translocated too rapidly causing toxicity because of immediate excess availability of the liquid. Phytotoxicity is a major problem especially if concentrated nutrient solution is used. Phytotoxicity resulted after 24 to 48 hours of treatment of citrus trees injected with 1, 3 and 5 ml of each of 5% Fe and 8% Fe. Even with diluted solutions of 1 ml of 5% Fe with 4 ml of water and with 10 ml of water resulted in phytotoxicity in a navel orange tree after 48 hours. After about 12 hours of the treatment, the leaves of the treated plants started to fold upward and after a few days turned yellow-brown in color. The phytotoxicity is mainly due to the rapid absorption of the nutrient to the leaves in concentrations far in excess in the amount needed by the plant.

A need therefore remains for an effective, economical means of providing nutrients and pesticides, both water soluble and insoluble, at controlled rates to above-ground portions of trees without harmful side effects.

SUMMARY OF THE INVENTION

With the foregoing in mind, the present invention eliminates or substantially alleviates the shortcomings in the prior art methods of introduction of nutrient and pesticide treatment agents, or other such substances, into the transpiration flow of trees. Selected materials are separately prepared, then combined to provide all required correctional constituents incorporated into a single combined material for application to nutrient deficient and/or diseased trees.

The principal feature of this invention is the use of polyethylene glycols (PEGs). Polyethylene glycol is also referred to as polyoxyethylene (POE), and polyethylene oxide (PEO). The PEGs are a family of water-soluble polymers that share a common chemical structure, primarily a hydroxyl group at each end of a poly-ether chain that consists of several sub-units of oxyethylene (CHCHO). The family of PEGs features the general formula

where n is the average number of oxyethylene subunits (Gao, K. 1993. Polyethylene Glycol as an Embedment for Microscopy and Histochemistry, pp. 1–7). Some of the interesting characteristics that make the PEGs unique polymers include solubility in water, the ability to act as a solvent to dissolve many substances including some water-insoluble compounds and some highly polar chemicals, good stability, non-toxicity, and wide compatibility with other substances. Polyethylene glycols have high water solubility and, due to their ability to dissolve aromatic compounds, have been used as dispersants of many water insoluble medicinal and pharmaceutical chemicals (i.e., they enhance the solubility of these chemicals in aqueous systems). The higher molecular weight PEGs are more able to solubilize water-insoluble compounds than are the lower molecular weight PEGs.

A small solid plug is prepared comprising a combination of the required treatment agents with one or more of the PEG's, or with one of the fatty acid derivatives of PEG. The formulations used are of particular selected molecular weights (i.e., the PEG molecular weights are each associated with a corresponding melting point and solubility in water). Generally, the desired melting point should exceed the existing outside ambient temperature in order to facilitate handling. The molecular weight of PEG determines the rate at which the incorporated treatment agent will dissolve in contact with water in the tree sap to supply the treatment agent to the plant. The addition of treatment agents into the melted PEG results in a mixture which can be placed into a mold to solidify into a plug when allowed to cool to ambient temperature. The mold may be a cylindrical, elongate shape from which individual segments of desired length may be cut. Likewise, the mold may comprise multiple cavities each forming an individual plug of desired shape. The PEG plugs may then be pressed from the mold cavities and packaged for later use.

Each plug is then inserted into a bored hole made into the tree trunk. Each hole is preferably subsequently sealed with grafting wax. Each PEG plug slowly dissolves into the flow of tree sap, and the injected material is distributed to all parts of the tree.

THE DRAWINGS

Figure 7:
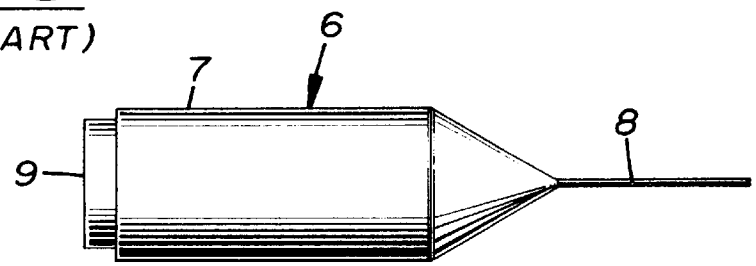

In the drawings, which represent the best mode presently contemplated for carrying out the invention, FIG. 1 is a side elevational view of a fragment of the trunk of a tree to be treated by the inventive injection method, indicating the holes into which the plugs of polyethylene glycol are inserted, drawn to a reduced scale;

FIG. 2 a, sectional pie cut of a portion of the trunk of FIG. 1, drawn to a larger scale than FIG. 1, while being at a reduced scale, showing one of the plugs and the hole into which it is inserted;

FIG. 3, a perspective view of an elongate mold for the plugs, along with said mold being segmented into individual lengths, from which the individual plugs are removed for treatment of the tree, drawn to a somewhat reduced scale;

FIG. 4, a side elevational view of a multiple cavity mold for the plugs partially cut away to shown internal cavity shape, drawn to somewhat reduced scale;

FIG. 5, a schematic representation of the preparation and molding of the plugs;

FIG. 6, a side elevational view of a prior art plastic cartridge into which a capsule containing treatment agent is placed prior to insertion of the cartridge into a hole in the tree trunk, drawn to approximately actual scale; and FIG. 7, a side elevation view of a prior art injector used to inject a liquid containing treatment agents into the tree trunk, drawn to approximately one-half scale.

DETAILED DESCRIPTION OF THE ILLUSTRATED EMBODIMENT

The present invention often involves the use of treatment agents such as iron compounds comprising iron citrate and iron ammonium citrate, mixed with pre-melted polyethylene glycol and cooled to form a solid. Iron citrates are often chosen because plans use citrates for the normal translocation of iron in the tissue, particularly the xylem of the tree trunk. Several other treatment agents are also suitable for mixing with PEG. (Table I.) Several other chemicals are also suitable for mixing with PEG. (Table I.)

TABLE I (A list of some of the treatment agents
that can be mixed with polyethylene glycol.)

| NUTRIENTS | PESTICIDES |
|---|---|
| Iron Salts | Insecticides |
| Zinc salt | Fungicides |
| Manganese salt | Bactericides |
| Magnesium salt | Larvicides |
| Nutrient Mixture | Rodenticides |
| Nutrients and/or | |
| Pesticides Mixtures | |

PEG is a clear viscous liquid or a solid, depending upon its molecular weight and temperature, which dissolves readily in water to form a transparent, non-toxic solution. It is commonly used in food and food handling, in cosmetics, and in medicine as a pharmaceutical aid (Budavri, S., 1989. The Merck Index, pp. 1204).

The molecular weight is selected for the PEG to liquify at a desired temperature (Table II) so as to facilitate manufacture of solid plugs 10 to insert into bores 11 about one to two inches deep drilled into the transpiration layer (the "sap" wood) 12 of the tree trunk (FIGS. 1 and 2). The plugs 10 comprise PEG and nutrients, insecticides and/or other treatment agents to correct nutritive deficiency and/or to treat and prevent tree diseases.

For example, to maintain PEG as a sold in hot climates, 25% PEG 1500 and 75% PEG 8000 may be mixed to achieve a melting point of approximately 70° C. The treatment agents comprising nutrients, insecticides, fungicides, growth regulators, or combinations of these substances in desired effective concentrations may be mixed into melted liquid PEG to be then poured into an elongate mold 13 of about ⅛ to ½ inch diameter, for example (FIG. 3). After the PEG mixture is solidified by cooling, the mold contains segments 14 of the desired length, each containing a plug 10 of the PEG and treatment agent.

TABLE II (Melting point temperatures of
PEG formulations at various molecular weights.)

| Molecular Weight | Melting Point |
|---|---|
| PEG  200 | Liquid at 0° C. |
| PEG  400 | 4–8° C. |
| PEG  600 | 20–25° C. |
| PEG 1500 | 44–48° C. |
| PEG 4000 | 54–58° C. |
| PEG 6000 | 56–63° C. |
| PEG 8000 | 67–71° C. |

The plugs 10 may then be removed by segmenting the mold 13 and inserted into bores 11 distributed about the circumference of the tree trunk 15, to be slowly but completely dissolved into the transpirational stream and carried to all tree parts (FIGS. 1 and 2).

The solubility of the treatment agent is controlled by the molecular weight of the PEG or PEG derivatives used. The higher molecular weight PEGs are better solvents than the lower molecular weight PEGs. For hot weather, a higher molecular weight PEG may be used and for cooler weather a lower molecular weight PEG may be used. The solubility of PEG is also affected by its molecular weight. The higher the molecular weight, the slower the dissolution rate in water. The highest molecular weight of PEG available (8000) may be used if it is desired to deliver the incorporated chemicals during a much longer period of time. When the higher molecular weight PEG is used with the desired treatment agent therein, the complete release inside the tree will be prolonged up to 7 to 10 days.

To obtain plugs to use for iron deficiency, for example, the following mixture is used:

PEG—30 grams

Iron citrate or Iron Ammonium Citrate—18 grams

Manganese Sulfate—0.7 grams

Zinc Sulfate—0.6 grams

The mixture may, for example, be poured into an elongate ⅜ inch cylindrical mold 13, to solidify and be cut into segments 14 about ⅝ inch long, from each of which the plugs 10 are removed (FIG. 3). Alternately, a mold 13A with multiple plug cavities may be used (FIG. 4). Each plug contains about 0.1 grams of elemental iron, 8 mg of elemental zinc, and 8.3 mg of elemental manganese. Such plugs when put into water dissolve completely in 30 minutes.

Applicant has used the plugs successfully on many species of trees, including apple, peach, citrus, pin oak, pines, pear, avocado, poplar and black locust. After 3–5 days the plug typically completely dissipates and translocates to the leaves. Procedures used are indicated in Table III for iron supplementation.

TABLE III

1. Calculate the number of plugs of iron per tree, depending on the tree size, foliation of leaves and condition (severity of deficiency). (Each plug 10 requires a separate hole 11.)
2. Bore the appropriate number of holes 11 about 2 feet above the ground on a downward slant in the trunk 15. Each plug 10 requires a separate hole 11. The height of the subsequent holes are offset from the first hole slightly to avoid weakening the trunk. The diameter of the hole is about 0.4 inches (0.95 cm), depending on the size of the tree and 2 inches (5 cm) deep. Four or more holes may be used for very large trees. Plugs of Phyto-Plus[R] injection iron is enough to increase the iron content of 35 lbs of leaves by 50 ppm on a dry weight basis.

Very large tree (trunk over 2 feet in diameter).

| | |
|---|---|
| Heavily foliated (100% leaves) | 20 plugs |
| Moderately foliated (75% leaves) | 15 plugs |

Large tree (trunk 18 inches).

| | |
|---|---|
| Heavily foliated (100% leaves) | 8 plugs |
| Moderately foliated (75% leaves) | 5 plugs |

Medium tree (trunk 6–9 inches).

| | |
|---|---|
| (Mature fruit and nut trees, slight Iron chlorosis) | 4 plugs |
| Half foliated | 2 plugs |

Small tree (trunk 3–4 inches)

| | |
|---|---|
| Fully foliated | 2 plugs |
| Half foliated, chlorotic | 1.5 plugs |
| Partially foliated, severely chlorotic | 1 plug |

3. Place a plug in each hole and seal all holes with grafting wax.
4. If in doubt as to proper dosage, add less than that indicated and repeat with additional iron later. In severely chlorotic trees use a small dose and repeat after several weeks. Dose is dependent on leaf mass and not trunk diameter.
5. Re-grening starts within a week and the plugs can be used on most trees with no injury.
6. Alcohol or flame sterilization of steel bits is recommended in areas of bacterial or viral infection.
7. Procedures have been used successfully in ornamental, citrus, mangos, pear, apple, peach, etc.

Other examples of use of the PEG plugs 10 follow below:

An insecticide (Orthene, Dimethoate, etc.) for injection into ornamental trees is incorporated with PEGs of 1500 and 8000 molecular weight at a 1–5 ratio. The insecticide used may be Orthene PCO formula II (EPA Est. 39578-TX1). This mixture is effective against ants, cockroaches, weevils, mites, and aphids for example. Three-fourths (¾) of a gram of Orthene PCO formula II (Active Ingredients is 96% Acephate o.s.—Dimethyl Aacetophospor—amidothioate) is added to each gram of PEG. Both PEG and Orthene melt at 70° C. so the mixture is clear. After pouring the mixture, for example, into an elongate ⅜ inch diameter mold and cooling, the mold is cut into segments of about ¾ inch length and the plugs removed from each. Each plug contains about 0.75 grams of Orthene. This plug readily dissolves in water in about 15 minutes. The number of plugs is dependent upon tree size, and is selected as outlined above.

An 18 year old navel orange tree having a trunk diameter 9 inches infested with aphids was treated with 4 plugs of PEG-Orthene PCO formula mixture 1 to 0.75. The plugs were equally spaced around the trunk. The treatment site was covered with grafting wax. The plugs were totally dissolved in 4 days. The orange tree was free of aphids ten days after the treatment and showed no signs of phytotoxicity.

An 18 year old chlorotic navel orange tree having a trunk diameter of 9 inches was treated with 4 plugs of PEG-Ferric ammonium citrate mixture having 0.1% iron. The treatment site was covered with grafting wax. The plugs were totally dissolved in 5 days. The symptoms of iron chlorosis gradually disappeared and within 4 weeks the leaves were noticeably greener. After 2 months from the injection the tree fully recovered. The tree did not show any sign of phytotoxicity.

A pine tree having a 20 inch trunk diameter infested with pine bark beetles was treated with eight plugs of PEG-Orthene PCO formula II mixture (PEG: Orthene was 1:0.75). The plugs were equally spaced around the trunk 3 inches above the ground. The plugs were totally dissolved in 4 days. Two weeks later, the outer layer of the bark was peeled off and a few tunnels were present with the dead beetles and larvae inside.

FIG. 5 shows the plug-making process. Polyethylene glycol powders 17 of the desired molecular weights are combined in a heating tank 18 and melted to form a PEG liquid of the desired molecular weight. The desired treatment agents 19 (e.g. nutrients and pesticides) are added to the PEG liquid in mixer 21 and the mixture 22 further heated in heating tank 23 to combine the liquid PEG and the treatment agents 19. The heat should be sufficiently high to transform the PEG 17 and treatment agent 19 to a slurry or paste 22, but not high enough to degrade or decompose the treatment agents 19. After about 15 minutes of heating, the paste may be poured into a mold with the desired plug shape and size, for example, elongate cylindrical mold 13, and cooled. Approximate dimensions of the plugs are ½ to 1 inch in length and ⅛ to ½ inch in average diameter. If tapered plugs 10A are preferred, so as to wedge tightly into the holes 11, the multiple cavity mold 13A may be used (FIG. 4). Smaller size plugs are desirable for trees with 3 inch diameters or less and the bigger sizes for trees with diameters larger than 3 inches. The molded mixture is allowed to cool and harden for about an hour, before removal from the mold. This method may be used to make a variety of shapes and sizes of plugs.

The inventive apparatus may be embodied in other specific forms, and the method in other specific steps, without departing from the spirit or essential characteristics thereof. The present apparatus and method are therefore to be considered illustrative and not restrictive, the scope of the invention being indicated by the appended claims rather than by the foregoing description and all changes which come within the meaning and range of equivalency of the claims are therefore to be embraced therein.

What is claimed and desired to be secured by United States Letters Patent is:

1. A method of providing a tree with a steady stream of a treatment agent, comprising the steps:

providing a water soluble, generally homogeneous plug comprising polyethylene glycol of a molecular weight selected so as to be a solid at a predetermined ambient temperature and containing a treatment agent, which plug is not contained in a casing;

boring a hole for said plug into the transpirational portion of the trunk of the tree above the ground of such size as to receive said plugs; and inserting said plug into the hole such that said plug contacts the inner bore of the hole so as to completely dissolve at a generally steady rate and leaving no non-dissolving casing or other such non-dissolving material therein.

2. A method according to claim 1, wherein the plugs are constructed using the following steps:

providing a mold for the plug;

melting the polyethylene glycol and mixing in the desired treatment agent to form a melted mixture;

pouring the melted mixture into the mold and allowing the mixture to cool to a temperature below the melting point of the mixture; and separating the plug from the mold.

3. A method according to claim 1, wherein the treatment agent provides nutritional treatment to the tree.

4. A method according to claim 1, wherein the treatment agent provides medicinal treatment to the tree.

5. A method according to claim 1, wherein the treatment agent provides nutritional treatment to the tree and a second treatment agent provides medicinal treatment to the tree.

6. A method according to claim 1, wherein the molecular weight of the polyethylene glycol is selected to be within the range of 200 to 8,000 grams per mole, as required for the desired delivery rate of the treatment agent to the tree.

7. A method according to claim 1, wherein the treatment agent is substantially insoluble in water but soluble in polyethylene glycol.

8. A method according to claim 1, wherein the treatment agent will polymerize with the polyethylene glycol to form a new material having nutritional value to the tree, which treatment agent is delivered to the tree at a desired rate by selection of the molecular weight and solubility of the polyethylene glycol.

9. A method according to claim 6, wherein:

the plug is ⅛ to ½ inch in diameter; and the molecular weight of the polyethylene glycol is selected so that the period of delivery of the treatment agent to the tree is within 2 to 10 days.

10. A method according to claim 4, wherein the treatment agent comprises a pesticide which contains dimethyl aacetophospor-amidothioate.

11. A method according to claim 4, wherein the treatment agent is dimethoate.

12. A method according to claim 3, comprising the treatment agents iron citrate, manganese sulfate, and zinc sulfate.

* * * * *